United States Patent [19]

Cameron

[11] Patent Number: 5,612,333
[45] Date of Patent: Mar. 18, 1997

[54] ANTIVIRAL COMBINATIONS

[75] Inventor: Janet M. Cameron, Greenford, Great Britain

[73] Assignee: Glaxo Group Limited, Great Britain

[21] Appl. No.: 356,322

[22] PCT Filed: Jul. 13, 1993

[86] PCT No.: PCT/EP93/01847

§ 371 Date: Dec. 29, 1994

§ 102(e) Date: Dec. 29, 1994

[87] PCT Pub. No.: WO94/02155

PCT Pub. Date: Feb. 3, 1994

[30] Foreign Application Priority Data

Jul. 16, 1992 [GB] United Kingdom ............ 9215178

[51] Int. Cl.$^6$ .................... A61K 31/55; A61K 31/505
[52] U.S. Cl. .......................... 514/220; 514/274
[58] Field of Search ..................... 514/274, 220

[56] References Cited

FOREIGN PATENT DOCUMENTS

| | | |
|---|---|---|
| WO-A-9117159 | 11/1991 | European Pat. Off. . |
| 9117159 | 11/1991 | WIPO ............ A61K 31/505 |

OTHER PUBLICATIONS

Merluzzi et al 1990, Science vol. 250 pp. 1411–1413.
Goldman et al., *Proc. Natl. Acad. Sci. USA*, vol. 88, No. 15, Aug. 1991, 6863–6867.
Flexner, *Curr. Opin. Infect. Dis.*, vol. 5/6, May 1992, 798–805.
Declercq, *AIDS Res. Hum. Retrovirus*, vol. 8, No. 2, Feb. 1992, 119–134.
Schinazi et al., *AIDS Res. Hum. Retrovirus*, vol. 8, No. 6, Jun. 1992, 963–990.
Tisdale et al., *Proc. Natl. Acad. Sci. USA*, vol. 90, Jun. 1993, 5653–5656.

*Primary Examiner*—Russell Travers
*Attorney, Agent, or Firm*—Bacon & Thomas

[57] ABSTRACT

Combinations of (2R, cis)-4-amino-1-(2-hydroxymethyl-1,3-oxathiolan-5-yl)-(1H)-pyrimidin-2-one or a pharmaceutically acceptable derivative thereof and 11-cyclopropyl-5,11-dihydro-4-methyl-6H-dipyrido[3,3-b;2$^1$,3$^1$-e][1,4]diazepin-6-one or a pharmaceutically acceptable derivative thereof, pharmaceutical formulations of such combinations and the use of such combinations and formulations to treat viral infections, in particular HIV infections, are described.

9 Claims, No Drawings

ANTIVIRAL COMBINATIONS

This application is a 371 of PCT/EP93/01897 filed on Jul. 13, 1993.

The present invention relates to combinations of antiviral agents. More specifically it is concerned with combinations of 1,3-oxathiolane nucleoside analogues with other antiviral agents, in particular agents effective against HIV. Human immunodefidency virus (HIV) causes a variety of clinical conditions including the acquired immune deficiency syndrome (AIDS) and chronic neurological disorders. Nucleosides such as AZT, ddC and ddI inhibit HIV replication in vitro, and appear to exert their antiviral activity on the virus-encoded reverse transcriptase enzyme after metabolism by the cell to their 5'-triphosphate derivatives.

AZT reduces morbidity and mortality in patients with AIDS. However, HIV infection of cells results in integration of the virus genome into the host chromosome, and so it has been necessary to continue AZT treatment for long periods of time. The consequences of long-term AZT therapy are associated bone-marrow toxicity and the appearance of AZT-resistant variants of HIV-1. Similarly, some AIDS patients treated with ddC develop peripheral neuropathy and ddI has been shown to induce pancreatitis and peripheral neuropathy.

The use of combinations of compounds may give rise to an equivalent antiviral effect with reduced toxicity, or an increase in drug efficacy if synergy between compounds occurs. Lower overall drug doses will possibly also reduce the frequency of occurrence of drug-resistant variants of HIV. Many different methods have been used to examine the effects of combinations of compounds acting together in different assay systems. All of these methods have limitations and for example, some methods have been applied to systems other than those for which they were derived. AZT demonstrates synergistic antiviral activity in vitro in combination with agents that act at HIV-1 replicative steps other than reverse transcription, including recombinant soluble CD4 castanospermine and recombinant interferon alpha. However, it must be noted that combinations of compounds can give rise to increased cytotoxicity. AZT and recombinant interferon alpha have an increased cytotoxic effect on normal human bone marrow progenitor cells.

The compound (2R, cis)-4-amino-1-(2-hydroxymethyl-1,3-oxathiolan-5-yl)-(1H)-pyridmidin-2-one, also known as 3TC is currently undergoing clinical trials for the treatment of conditions associated with infection by HIV.

We have now found that 3TC exhibits unexpected advantages when used in combination with certain non-nucleoside inhibitors of HIV.

There is thus provided in a first aspect of the invention a combination comprising 3TC or a pharmaceutically acceptable derivitive thereof and nevirapine or a pharmaceutically acceptable derivative thereof.

Nevirapine has the chemical name 11-cyclopropyl-5,11-dihydro-4-methyl-6H-dipyrido[3,3-b;2$^1$,3$^1$-e][1,4]diazepin-6-one and is also known as BI-RG-587.

3TC will normally be provided substantially free of the corresponding (+)-enantiomer, that is to say no more than about 5% w/w of the (+)-enantiomer, preferably no more than about 2%, in particular less than about 1% w/w will be present.

By "a pharmaceutically acceptable derivative" is meant any pharmaceutically acceptable salt, ester, or salt of such ester, of a parent compound or any other compound which, upon administration to the recipient, is capable of providing (directly or indirectly) the parent compound or an antivirally active metabolite or residue thereof.

It will be appreciated by those skilled in the art that 3TC may be modified to provide pharmaceutically acceptable derivatives thereof at functional groups in both the base moiety and at the hydroxymethyl group of the oxathiolane ring. Modification at all such functional groups are included within the scope of the invention. However of particular interest are pharmaceutically acceptable derivatives obtained by modification of the 2-hydroxymethyl group of the oxathiolane ring.

Preferred esters of 3TC include the compounds in which the hydrogen of the 2-hydroxymethyl group is replaced by an acyl function R—CO— in which the noncarbonyl moiety R of the ester is selected from hydrogen, straight or branched chain alkyl (e.g. methyl, ethyl, n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl-or aralkylsulphonyl (e.g. methanesulphonyl); amino acid esters (e.g. L-valyl or L-isoleucyl) and mono-, di- or tri-phosphate esters.

With regard to the above described esters, unless otherwise specified, any alkyl moiety present advantageously contains 1 to 16 carbon atoms, particularly 1 to 4 carbon atoms. Any aryl moiety present in such esters advantageously comprises a phenyl group.

In particular the esters may be a $C_{1-16}$alkyl ester, an unsubstituted benzyl ester or a benzyl ester substituted by at least one halogen (bromine, chlorine, fluorine or iodine), $C_{1-6}$alkyl, $C_{1-6}$alkoxy, nitro or trifluoromethyl groups.

Pharmaceutically acceptable salts of 3TC include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4^+$ (where R is $C_{1-4}$alkyl) salts.

3TC is either synergistic with the second component of the combination and/or reduces the cytotoxic effects of the second component.

The advantageous effects of 3TC and nevirapine are realised over a wide ratio for example 1:250 to 250:1 preferably 1:50 to 50:1, particularly about 1:10 to 10:1 by weight. Conveniently each compound will be employed in the combination in an amount at which it exhibits antiviral activity when used alone.

It is expected that the present combinations will be generally useful against viral infections or virus-associated tumours in humans, and the method of their use to inhibit viral infectivity or tumour growth in vitro or in vivo is also within the scope of the present invention.

Thus there is provided in a second aspect a method for the treatment of a viral infection in a mammal, including man, comprising co-administration of 3TC or a pharmaceutically acceptable derivative thereof and nevirapine or a pharmaceutically acceptable derivative thereof.

It will be appreciated that 3TC and nevirapine may be administered either simultaneously (either separately or in combination) or sequentially. If administration is sequential, the delay in administering the second of the active ingredients should not be such as to lose the benefit of any synergistic effect of the combination. Preferably administration will be simultaneous.

It will be appreciated by those skilled in the art that reference herein to treatment extends to prophylaxis as well as the treatment of established infections or symptoms.

It will be further appreciated that the amount of a combination of the invention required for use in treatment will vary not only with the particular compounds selected but also with the route of administration, the nature of the condition being treated and the age and condition of the patient and will be ultimately at the discretion of the attendant physician or veterinarian. In general however a suitable dose will be in the range of from about 1 to about 750 mg/kg e.g. from about 10 to about 75 mg/kg of bodyweight per day, such as 3 to about 120 mg per kilogram body weight of the recipient per day, preferably in the range of 6 to 90 mg/kg/day, most preferably in the range of 15 to 60 mg/kg/day of each of the active ingredients of the combination.

The desired dose may conveniently be presented in a single dose or as divided doses administered at appropriate intervals, for example as two, three, four or more sub-doses per day.

The combination is conveniently administered in unit dosage form; for example containing 10 to 1500 mg, conveniently 20 to 1000 mg, most conveniently 50 to 700 mg of each active ingredient per unit dosage form.

Ideally the combinations should be administered to achieve peak plasma concentrations of each of the active compound of about 1 to about 75 μM, preferably about 2 to 50 μM, most preferably about 3 to about 30 μM. This may be achieved, for example, by the intravenous injection of a 0.1 to 5% solution of the active ingredients, optionally in saline, or orally administered as a bolus containing about 1 to about 100 mg of each active ingredient. Desirable blood levels may be maintained by a continuous infusion to provide about 0.01 to about 5.0 mg/kg/hour or by intermittent infusions containing about 0.4 to about 15 mg/kg of each active ingredient.

While it is possible that, for use in therapy, the active ingredients of the combination may be administered as the raw chemical it is preferable to present combinations as a pharmaceutical formulation.

The invention thus further provides a pharmaceutical formulation comprising 3TC or a pharmaceutically acceptable derivative thereof and nevirapine or a pharmaceutically acceptable derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carders or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrates, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active .ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one more dispersing agents, solubilising agents or suspending agents. Liquid sprays are conveniently delivered from pressurised packs.

For administration by inhalation the compounds according to the invention are conveniently delivered from an insufflator, nebuliser or a pressurised pack or other convenient means of delivering an aerosol spray. Pressurised packs may comprise a suitable propellant such as dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

3TC may be obtained as described in International Patent Application No. WO91/17159.

Nevirapine may be obtained as described in Science, 28, 1411–1414.

The following examples illustrate the invention but are not intended as a limitation thereof.

EXAMPLE 1

Antiviral Activities Alone or in Combination

Compounds are first serially-diluted in 2-fold decrements in 96-well microtitre plates. Chequerboard titrations are prepared by mixing 25 µl aliquots from each compound dilution both alone or in combination (to a final volume of 50 µl in new 96-well microtitre plates). Aliquots of MT-4 cells ($10^6$ cells/ml) in RPMI 1640 growth medium are infected with HIV-1 strain RF at a moi of $2\times10^{-3}$ infectious doses/cell. Virus is adsorbed at room temperature for 90 minutes, after which the cells are washed in RPMI 1640 growth medium to remove unadsorbed virus and resuspended at $10^6$ cells/ml in RPMI 1640 growth medium. 50 µl of infected cell suspension are inoculated into wells containing compound or growth medium only. 50 µl of mock-infected cell suspension are inoculated into wells not containing compound. The plates are then incubated for 7 days at 37° C. in 5% $CO_2$/air.

After incubation, 10 µl of 3-[4,5-dimethyl thiazol-2-yl]-2,5- diphenyltetrazolium bromide (MTT) at 7.5 mg/ml are added to all wells and the plates incubated for a further 90 minutes at 37° C. 150 µl of 10% (v/v) Tdton X-100 in isopropanol are then added and the cells resuspended. After 15 minutes at room temperature the plates are analysed in a Multiskan MC (Flow Laboratories, Irvine, UK) reader at 405 nm. Conversion of yellow MTT to its formazan derivative is maximum in the uninfected untreated cells, and absent in untreated infected cells.

Dose-response curves are plotted for each compound alone (IC50% values) and for reciprocal titrations of each compound at a fixed concentration of the second compound. Isobolograms of all compound combinations giving IC50% values are plotted.

If the, IC50% values of compound combination lies on a line joining the IC50% values of each compound on its own, then the two compounds act additively. If the combination IC50% lie to the left of the line, the compounds are acting synergistically.

EXAMPLE 2

Cytotoxicities of Compounds Alone and in Combination.

Cytotoxicity is determined by examination of the cells employed in Example 1 following drug treatment and/or by comparing the cytotoxicities of 3TC and the non-nucleoside HIV inhibitors alone and in combination (at µg/ml ratios of 1:1, 1:5 and 5:1) in uninfected peripheral blood lymphocytes and an established T-lymphocyte cell line; cytotoxicity is measured using a [$^3$H]-thymidine uptake assay.

I claim:

1. A combination comprising about 150 mg (2R,cis)-4-amino-1-(2-hydroxymethyl-1,3-oxathiolan-5-yl)-(1H)-pyrimidin-2-one or a pharmaceutically acceptable salt or ester thereof and about 200 mg 11-cyclopropyl-5, 11-dihydro-4-methyl-6H-dipyrido[3,3-b;$2^1$,$3^1$-e][1,4]diazepin-6-one or a pharmaceutically acceptable salt or ester thereof.

2. A combination comprising a first compound which is (2R, cis)-4-amino-1-(2-hydroxymethyl-1,3-oxathiolan-5-yl)-(1H)-pyrimidin-2-one and a second compound which is 11-cyclopropyl-5,11-dihydro-4-methyl-6H-dipyrido[3,3-b;$2^1$,$3^1$-e][1,4]diazepin-6-one; said combination containing said first and second compounds in effective amounts to achieve after oral administration peak plasma concentrations of from 3 to about 30 µM of each of the compounds and to achieve a plasma molar ratio of said first compound to said second compound of about 1:1.

3. A pharmaceutical formulation comprising a combination as defined in claim 1 together with a pharmaceutically acceptable carrier thereof.

4. A method for the treatment of a mammal suffering from or susceptible to infection by HIV comprising co-administration of about 150 mg (2R,cis)-4-amino-1-(2-hydroxymethyl-1,3-oxathiolan-5-yl)-(1H)-pyrimidin-2-one or a pharmaceutically acceptable salt or ester thereof and about 200 mg 11-cyclopropyl-5,11-dihydro-4-methyl-6H-dipyrido[3, 3-b;$2^1 3^1$-e][1,4]diazepin-6-one or a pharmaceutically acceptable salt or ester thereof.

5. A method according to claim 4, wherein administration is sequential.

6. A method according to claim 4, wherein administration is simultaneous.

7. A method according to claim 4, wherein the dosages are administered twice a day.

8. A method according to claim 4, wherein said mammal is a man.

9. A pharmaceutical formulation comprising a combination as defined in claim 2 together with a pharmaceutically acceptable carrier therefor.

* * * * *